(12) United States Patent
Nishiyama et al.

(10) Patent No.: US 9,877,635 B2
(45) Date of Patent: Jan. 30, 2018

(54) IMAGE PROCESSING DEVICE, IMAGE PROCESSING METHOD, AND COMPUTER-READABLE RECORDING MEDIUM

(71) Applicant: OLYMPUS CORPORATION, Tokyo (JP)

(72) Inventors: Takeshi Nishiyama, Akishima (JP); Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/370,492

(22) Filed: Dec. 6, 2016

(65) Prior Publication Data

US 2017/0079506 A1 Mar. 23, 2017

Related U.S. Application Data

(63) Continuation of application No. PCT/JP2015/062741, filed on Apr. 27, 2015.

(30) Foreign Application Priority Data

Sep. 22, 2014 (JP) .................................. 2014-193104

(51) Int. Cl.
*A61B 5/00* (2006.01)
*A61B 1/00* (2006.01)
*A61B 1/04* (2006.01)

(52) U.S. Cl.
CPC ........ *A61B 1/00009* (2013.01); *A61B 1/0005* (2013.01); *A61B 1/00045* (2013.01); *A61B 1/041* (2013.01); *A61B 1/00016* (2013.01)

(58) Field of Classification Search
CPC .................................... A61B 1/00; A61B 5/00
See application file for complete search history.

(56) References Cited

U.S. PATENT DOCUMENTS 8,854,444 B2   10/2014  Kobayashi et al.
2007/0060798 A1  3/2007  Krupnik et al.

FOREIGN PATENT DOCUMENTS

JP   2006280792   *   4/2005   ............... A61B 1/00
JP   2006-280792 A    10/2006
(Continued)

OTHER PUBLICATIONS

International Search Report dated Jun. 2, 2015 issued in PCT/JP2015/062741.

*Primary Examiner* — Behrooz Senfi
*Assistant Examiner* — Maryam Nasri
(74) *Attorney, Agent, or Firm* — Scully, Scott, Murphy & Presser, P.C.

(57) ABSTRACT

An image processing device includes a processor including hardware. The processor is configured to: identify an image selected according to a user input operation received by an input device, from among a plurality of first images acquired by a capsule endoscope, as an identified image; determine whether or not the identified image is one of a plurality of second images acquired during a reciprocating movement of the capsule endoscope; and in response to the identified image being determined to be one of the plurality of second images, extract an image acquired in a first forward path or a last forward path of the reciprocating movement from among the plurality of second images.

7 Claims, 15 Drawing Sheets

(56) References Cited

FOREIGN PATENT DOCUMENTS

| | | |
|---|---|---|
| JP | 2009-508567 A | 3/2009 |
| JP | 2009-089910 A | 4/2009 |
| JP | 2013-085593 A | 5/2013 |
| WO | WO 2012/042986 A1 | 4/2012 |

* cited by examiner

| MOTION INFORMATION | ROW / TIME PARAMETER | 1 | 2 | ... | i-4 | i-3 | i-2 | i-1 | i | i+1 | i+2 | i+3 | i+4 | i+5 | ... | n |
|---|---|---|---|---|---|---|---|---|---|---|---|---|---|---|---|---|
| FORWARD | FIRST ROW | 0 | 2 | | 106 | 108 | 112 | 110 | 104 | 102 | | | | | | |
| REVERSE | SECOND ROW | | | | | | | | | | 104 | | | | | |
| - | THIRD ROW | | | | | | | | | | | | | | | |
| FORWARD | FOURTH ROW | | | | | | | | | | | 104 | 106 | 110 | | 998 |

RECIPROCATING MOVEMENT SECTION (i-4 to i+5)

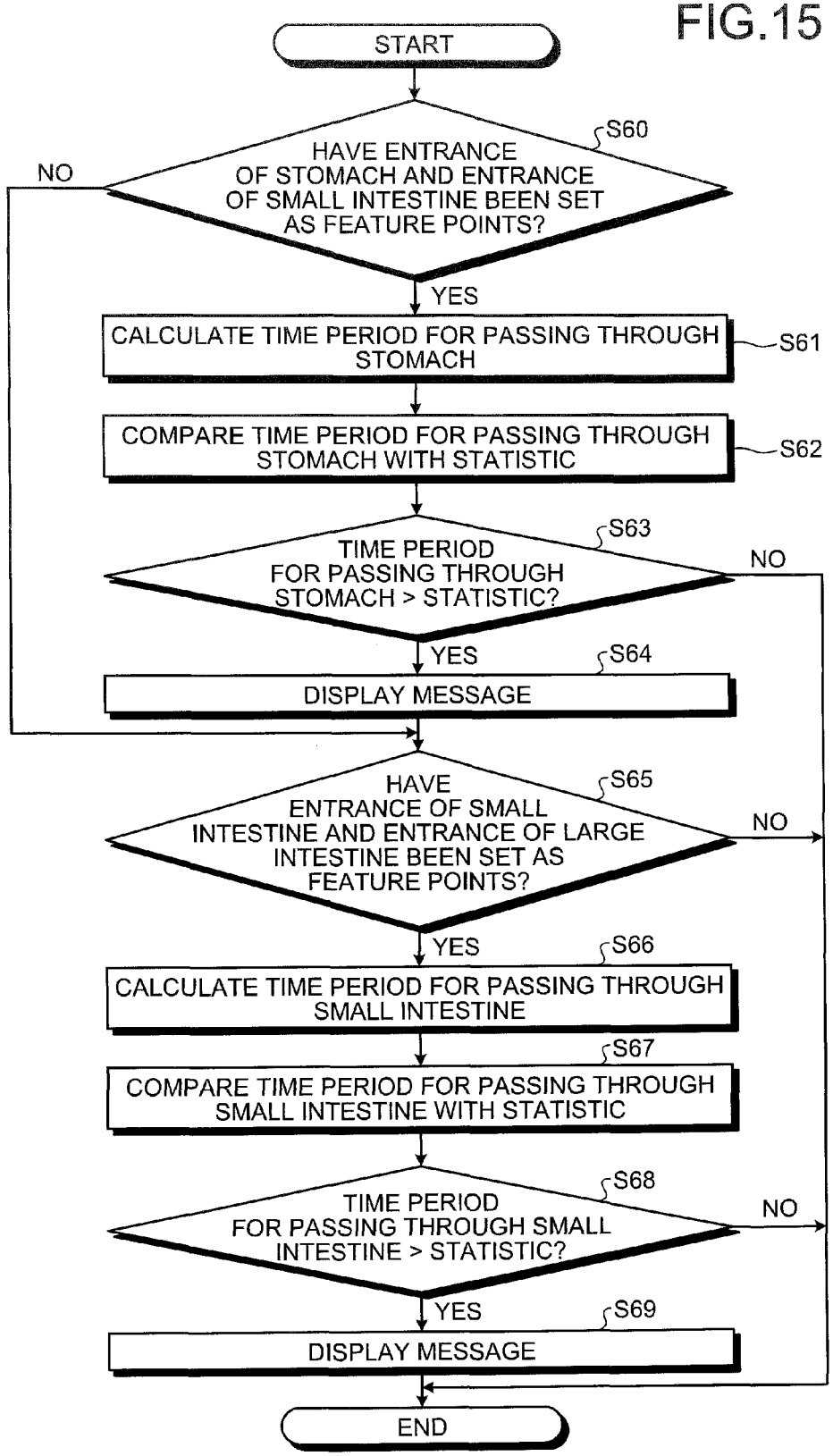

IMAGE PROCESSING DEVICE, IMAGE PROCESSING METHOD, AND COMPUTER-READABLE RECORDING MEDIUM

CROSS-REFERENCE TO RELATED APPLICATIONS

This application is a continuation of PCT international application Ser. No. PCT/JP2015/062741 filed on Apr. 27, 2015 which designates the United States, incorporated herein by reference, and which claims the benefit of priority from Japanese Patent Application No. 2014-193104, filed on Sep. 22, 2014, incorporated herein by reference.

BACKGROUND

1. Technical Field

The disclosure relates to an image processing device, an image processing method, and a computer-readable recording medium, which display an image acquired by a capsule endoscope that is introduced into a subject and captures an image inside the subject.

2. Related Art

In recent years, in the field of endoscope, an examination using a capsule endoscope that is introduced into a subject such as a patient and captures an image is known. The capsule endoscope is a device where an imaging function, a wireless communication function, and the like are included in a capsule-shaped casing formed into a size that can be introduced into a digestive tract of the subject. The capsule endoscope sequentially and wirelessly transmits image data generated by capturing an image inside the subject to the outside of the subject. The image data wirelessly transmitted from the capsule endoscope is once accumulated in a receiving device provided outside the subject, is transferred (downloaded) from the receiving device to an image display device such as a workstation, and is variously image-processed in the image display device.

When observing a series of images acquired in this way, normally, a user such as a doctor sets an image including a feature portion such as an organ boundary and a surgical scar as a feature point while generally browsing the images by reproducing the images as a moving image or continuously reproducing still images. Thereafter, the user performs diagnosis such as extracting a desired image based on the set feature point and observing the image in detail or determining a motor function of an organ based on a difference between imaging times corresponding to a moving time of the capsule endoscope from one feature point to another feature point among a plurality of set feature points. Therefore, to perform a correct diagnosis, it is important to set feature points to an appropriate image.

As a technique related to extracting an image from a series of images acquired by a capsule endoscope, Japanese Laid-open Patent Publication No. 2006-280792 A discloses a technique to calculate a correlation value of a plurality of pixel areas that are set on each image of a series of images, to calculate a motion vector of the plurality of pixel areas, to detect a continuous image group in which images having a correlation value of a plurality of pixel areas between adjacent images is greater than or equal to a predetermined value, continuously appear, to identify one or more representative images from among the continuous image group, and to display the one or more representative images at a display frame rate different from that of images other than the one or more representative images.

SUMMARY

In some embodiments, an image processing device includes a processor including hardware. The processor is configured to: identify an image selected according to a user input operation received by an input device, from among a plurality of first images acquired by a capsule endoscope, as an identified image; determine whether or not the identified image is one of a plurality of second images acquired during a reciprocating movement of the capsule endoscope; and in response to the identified image being determined to be one of the plurality of second images, extract an image acquired in a first forward path or a last forward path of the reciprocating movement from among the plurality of second images.

In some embodiments, an image processing method includes: identifying an image selected according to a user input operation, from among a plurality of first images acquired by a capsule endoscope, as an identified image; determining whether or not the identified image is one of a plurality of second images acquired during a reciprocating movement of the capsule endoscope; and in response to the identified image being determined to be one of the plurality of second images, extracting an image acquired in a first forward path or a last forward path of the reciprocating movement from among the plurality of second images.

In some embodiments, a non-transitory computer-readable recording medium recording an image processing program is provided. The program causes an image processing device to execute: identifying an image selected according to a user input operation, from among a plurality of first images acquired by a capsule endoscope, as an identified image; determining whether or not the identified image is one of a plurality of second images acquired during a reciprocating movement of the capsule endoscope; and in response to the identified image being determined to be one of the plurality of second images, extracting an image acquired in a first forward path or a last forward path of the reciprocating movement from among the plurality of second images.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 10 is a schematic diagram illustrating an example of a time series index;

FIG. 15 is a flowchart illustrating organ function determination processing performed by the image display device illustrated in FIG. 14.

DETAILED DESCRIPTION

Figure 1:
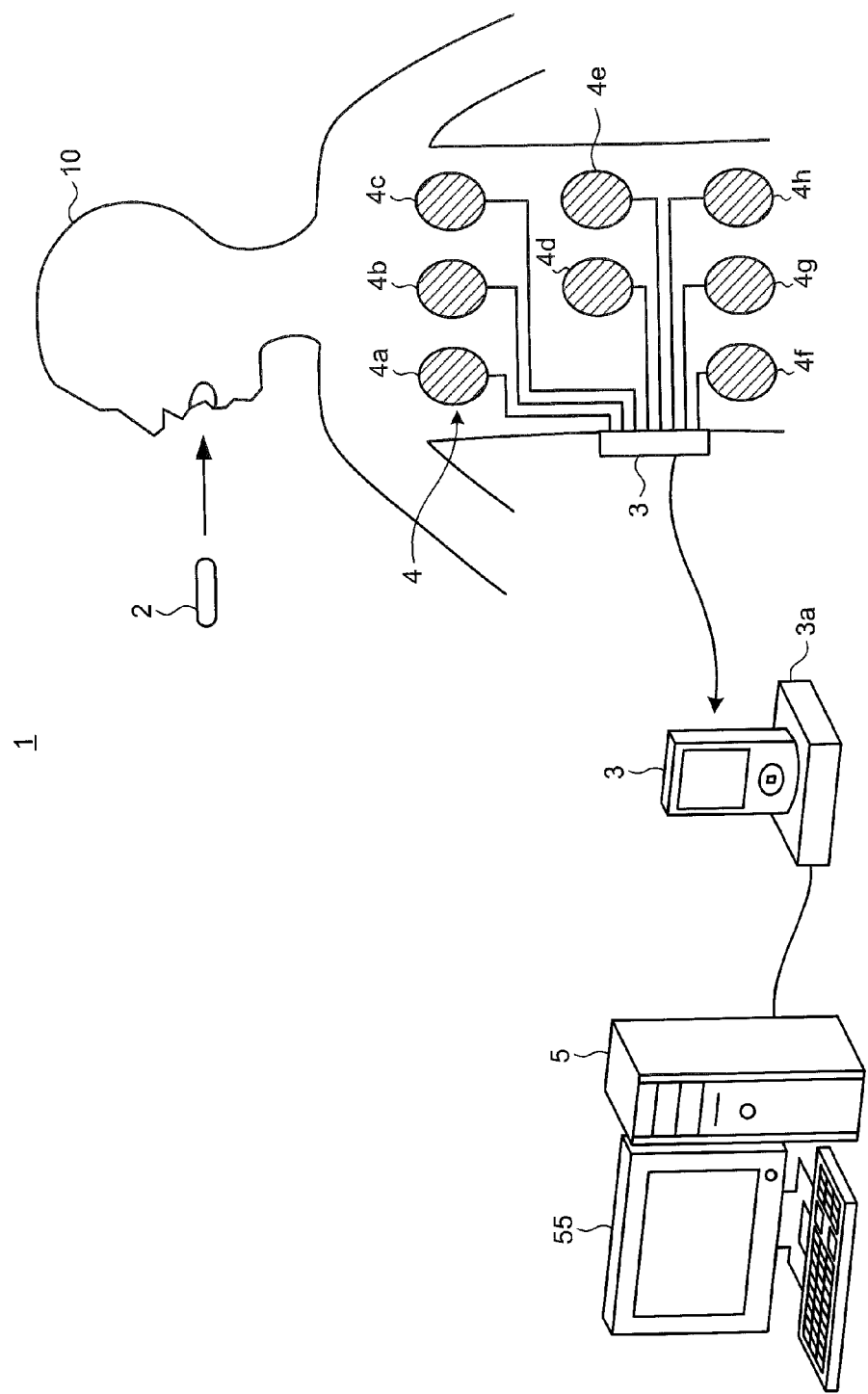
FIG. 1 is a schematic diagram illustrating a schematic configuration of a capsule endoscope system including an image display device according to a first embodiment of the present invention.

Hereinafter, an image display device, an image display method, and an image display program according to embodiments of the present invention will be described with reference to the drawings. The present invention is not limited by the embodiments. In the drawings, the same components are denoted by the same reference numerals.

First Embodiment

FIG. 1 is a schematic diagram illustrating a schematic configuration of a capsule endoscope system including an image display device according to a first embodiment of the present invention. A capsule endoscope system 1 illustrated in FIG. 1 includes a capsule endoscope 2 which generates image data by being introduced into a subject 10 and capturing an image in the subject 10 and transmits the image data by superimposing the image data on a wireless signal, a receiving device 3 that receives the wireless signal transmitted from the capsule endoscope 2 through a receiving antenna unit 4 attached to the subject 10, and an image display device 5 that receives the image data from the receiving device 3, performs predetermined image processing on the image data, and displays an image.

Figure 2:
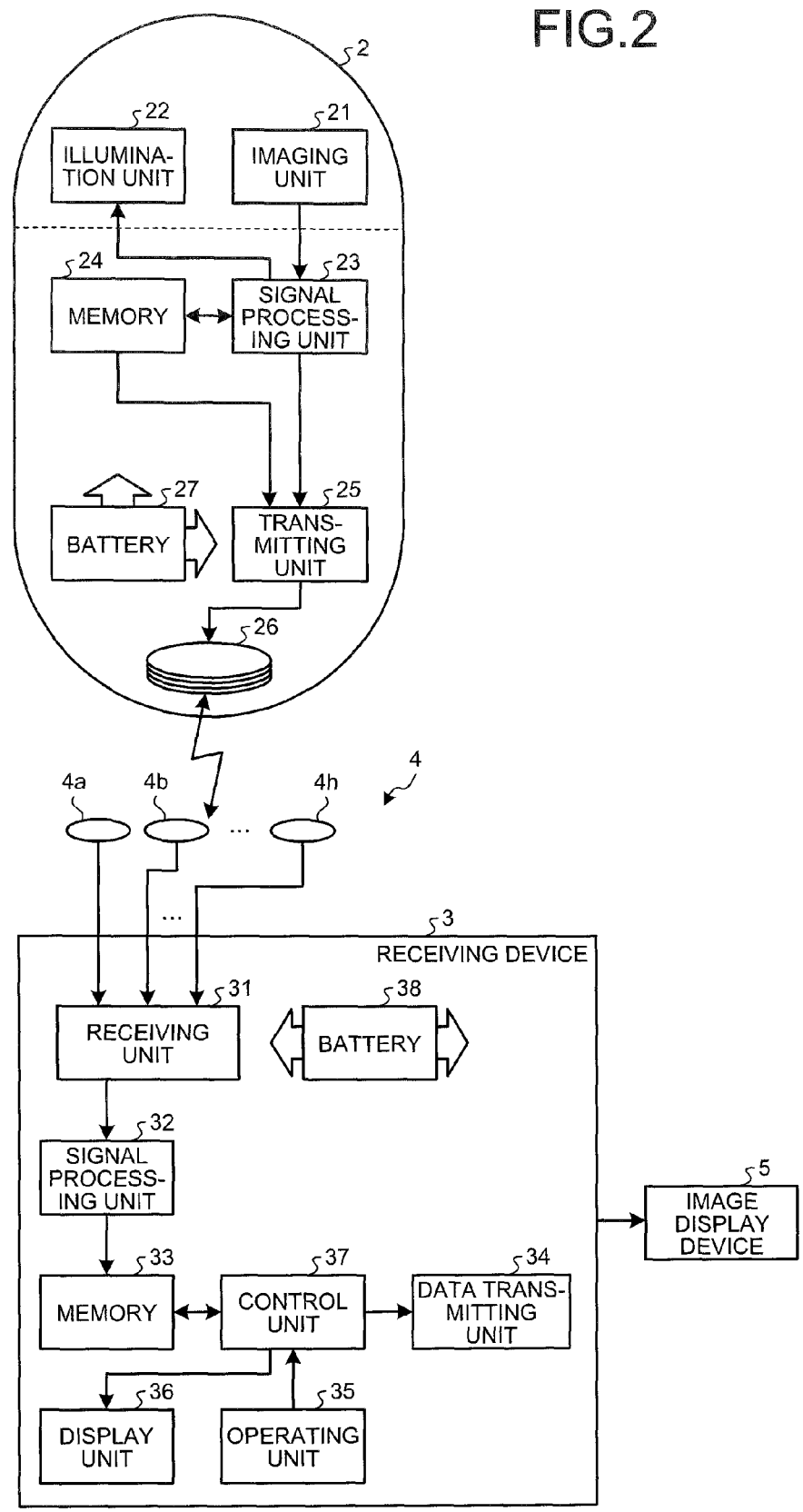
FIG. 2 is a diagram illustrating a schematic configuration of a capsule endoscope and a receiving device illustrated in FIG. 1.

FIG. 2 is a block diagram illustrating a schematic configuration of the capsule endoscope 2 and the receiving device 3.

The capsule endoscope 2 is a device that includes various components such as an imaging element in a casing having a capsule shape with a size that can be swallowed by the subject 10. The capsule endoscope 2 includes an imaging unit 21 that captures an image inside the subject 10, an illumination unit 22 that illuminates inside the subject 10, a signal processing unit 23, a memory 24, a transmitting unit 25, an antenna 26, and a battery 27.

The imaging unit 21 includes, for example, an imaging element such as CCD or CMOS that generates and outputs an imaging signal representing the inside of the subject 10 from an optical image formed on a light receiving surface and an optical system such as an objective lens arranged on a light receiving surface side of the imaging element. The illumination unit 22 is realized by a semiconductor light emitting element such as LED (Light Emitting Diode) or LD (Laser Diode) light source that emits light toward the subject 10 during imaging. The capsule endoscope 2 includes a circuit substrate where a drive circuit or the like that drives each of the imaging unit 21 and the illumination unit 22 is formed. The imaging unit 21 and the illumination unit 22 are fixed to the circuit substrate in a state in which the imaging unit 21 and the illumination unit 22 face toward the outside from one end portion of the capsule endoscope 2.

In FIG. 2, the imaging unit 21 and the illumination unit 22 are provided in one end portion of the capsule endoscope 2, so that an image on one side as seen from the capsule endoscope 2 can be captured. However, a plurality of imaging units 21 and illumination units 22 may be provided and a plurality of directions, for example, forward and backward directions or direct-viewing and side-viewing directions, may be defined as directions in which imaging can be performed.

The signal processing unit 23 controls each unit in the capsule endoscope 2, performs A/D conversion of the imaging signal outputted from the imaging unit 21 to generate digital image data, and further performs predetermined signal processing on the image data.

The memory 24 temporarily stores various processing programs, modules, and routines, which are executed by the signal processing unit 23, and the image data signal-processed by the signal processing unit 23.

The transmitting unit 25 and the antenna 26 superimpose the image data stored in the memory 24 on a wireless signal along with related information and transmit the wireless signal to the outside.

The battery 27 supplies power to each unit in the capsule endoscope 2. It is assumed that the battery 27 includes a power supply circuit that boosts power supplied from a primary battery or a secondary battery such as a button battery.

The capsule endoscope 2 is swallowed by the subject 10 and then the capsule endoscope 2 sequentially captures images of biological regions such as esophagus, stomach, small intestine, and large intestine at predetermined time intervals, for example, at time intervals of 0.5 sec while being moved in the digestive tract of the subject 10 by peristaltic movement and the like of organs. The capsule endoscope 2 sequentially and wirelessly transmits image data and related information generated by the image capturing operation to the receiving device 3. The related information includes identification information such as, a serial number assigned to identify individual of the capsule endoscope 2.

The receiving device 3 receives the image data and the related information wirelessly transmitted from the capsule endoscope 2 through the receiving antenna unit 4 including a plurality of (in FIG. 1, eight) receiving antennas 4a to 4h. Each of the receiving antennas 4a to 4h is realized by using, for example, a loop antenna and is arranged to a predetermined position on an outside surface of the subject 10. As an example, each of the receiving antennas 4a to 4h is arranged to a position corresponding to an organ in the subject 10, which is a passage route of the capsule endoscope 2.

As illustrated in FIG. 2, the receiving device 3 includes a receiving unit 31, a signal processing unit 32, a memory 33, a data transmitting unit 34, an operating unit 35, a display unit 36, a control unit 37, and a battery 38. The receiving unit 31 receives the image data wirelessly transmitted from the capsule endoscope 2 through the receiving antennas 4a to 4h. The signal processing unit 32 performs predetermined signal processing on the image data received by the receiving unit 31. The memory 33 stores the image data on which signal processing is performed by the signal processing unit 32 and information related to the image data.

The data transmitting unit 34 is an interface that can be connected to a communication line such as USB, wired LAN, or wireless LAN. The data transmitting unit 34 transmits the image data and the related information stored in the memory 33 to the image display device 5, under control of the control unit 37. The operating unit 35 is used when a user inputs various setting information and the like of the receiving device 3.

The display unit 36 displays registration information (examination information, patient information, and the like) related to examination and various setting information inputted by a user. The control unit 37 controls operation of each unit in the receiving device 3. The battery 38 supplies power to each unit in the receiving device 3.

While the capsule endoscope 2 performs imaging, in other words, during a period from when the capsule endoscope 2 is swallowed by the subject 10 to when the capsule endoscope 2 is discharged, the receiving device 3 is attached to the subject 10 and carried by the subject 10. During the period, the receiving device 3 further adds related information such as reception intensity information and reception time information at each of the receiving antennas 4a to 4h at a timing when each image data is received to the image data received through the receiving antenna unit 4. Then, the receiving device 3 stores these image data and the related information in the memory 33. After the imaging of the capsule endoscope 2 is completed, the receiving device 3 is removed from the subject 10 and connected to the image display device 5. Then, the receiving device 3 transfers the image data and the related information stored in the memory 33 to the image display device 5. In FIG. 1, a cradle 3a is connected to a USB port of the image display device 5 and the receiving device 3 is set in the cradle 3a, so that the receiving device 3 is connected to the image display device 5.

The image display device 5 is configured by using, for example, a workstation or a personal computer. The image display device 5 performs predetermined image processing on an image in the subject 10 acquired through the receiving device 3 to generate an observation screen of a predetermined format and displays the observation screen.

Figure 3:
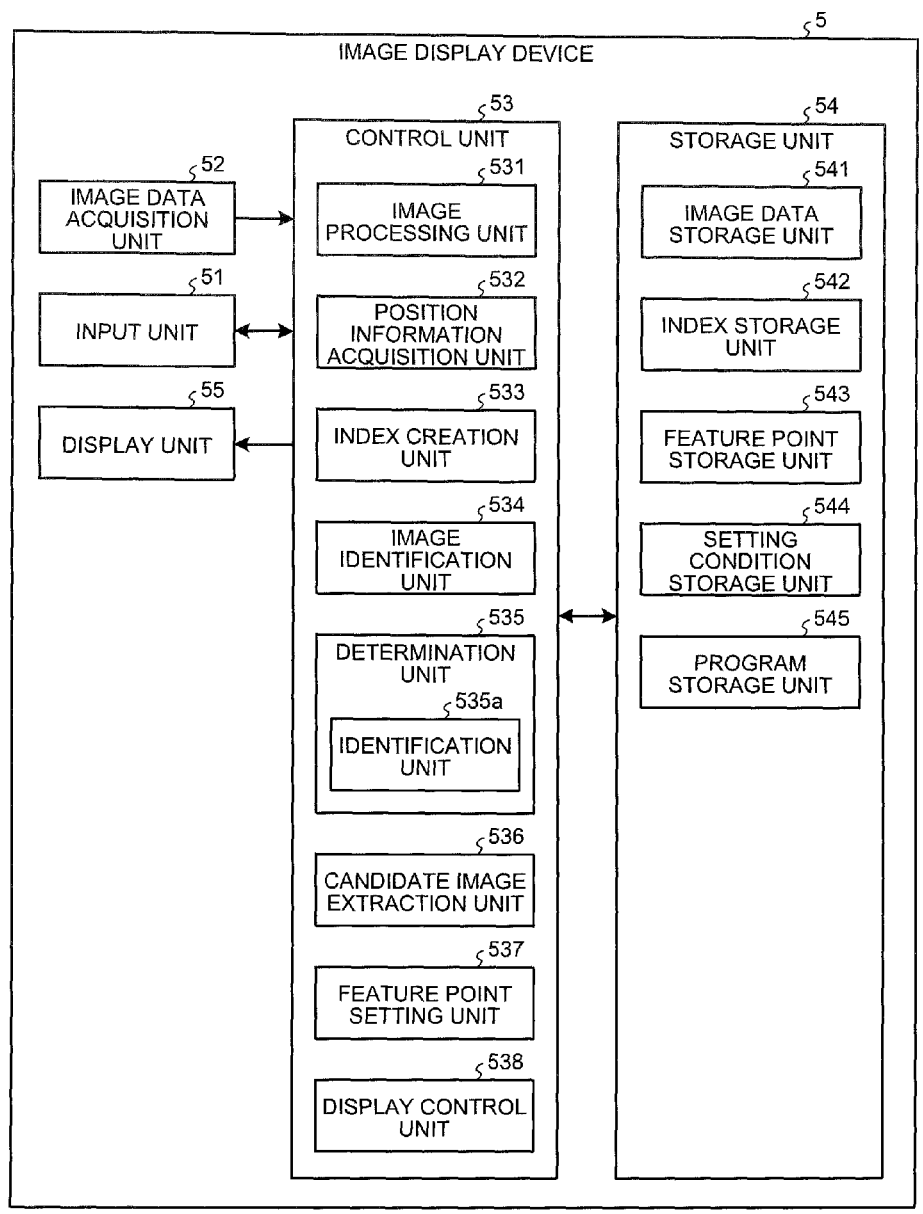
FIG. 3 is a block diagram illustrating a schematic configuration of the image display device illustrated in FIG. 1.

FIG. 3 is a block diagram illustrating a schematic configuration of the image display device 5. As illustrated in FIG. 3, the image display device 5 includes an input unit 51, an image data acquisition unit 52, a control unit 53, a storage unit 54, and a display unit 55.

The input unit 51 is realized by an input device, such as a keyboard, a mouse, a touch panel, and various switches. The input unit 51 inputs a signal according to an operation from outside by a user to the control unit 53.

The image data acquisition unit 52 is an interface that can be connected to a communication line such as USB, wired LAN, or wireless LAN, and includes a USB port, a LAN port, and the like. In the first embodiment, the image data acquisition unit 52 functions as a data acquisition unit that acquires the image data and the related information from the receiving device 3 through an external device, such as the cradle 3a, connected to the USB port and various communication lines.

The control unit 53 is realized by hardware such as a CPU and transmits an instruction and data to each unit included in the image display device 5 and controls the operation of the entire image display device 5 based on a signal inputted from the input unit 51, the image data acquired by the image data acquisition unit 52, and the like by reading various programs stored in the storage unit 54. In more detail, the control unit 53 includes an image processing unit 531, a position information acquisition unit 532, an index creation unit 533, an image identification unit 534, a determination unit 535, a candidate image extraction unit 536, a feature point setting unit 537, and a display control unit 538.

The image processing unit 531 generates display image data by performing image processing, such as white balance processing, demosaicing, color conversion processing, density conversion processing such as gamma conversion, smoothing processing by denoising and the like, and sharpening processing by edge enhancement and the like, on image data of a series of images obtained through the image data acquisition unit 52. Further, the image processing unit 531 performs predetermined image processing such as average color calculation processing that calculates an average color of each image based on the display image data.

The position information acquisition unit 532 detects a position of the capsule endoscope 2 when an image is captured, that is, a position of an object captured in an image, based on the reception intensity information when the receiving antennas 4a to 4h receive a wireless signal among the related information of the image data of each image. Hereinafter, the position of the capsule endoscope 2 while an image is captured is simply referred to as a capsule position. A detection method of the capsule position is not limited to a method based on the reception intensity of the wireless signal, but it is possible to use, for example, a method that uses magnetic field disclosed in JP 2009-226080 A and other various known methods.

Figure 4:
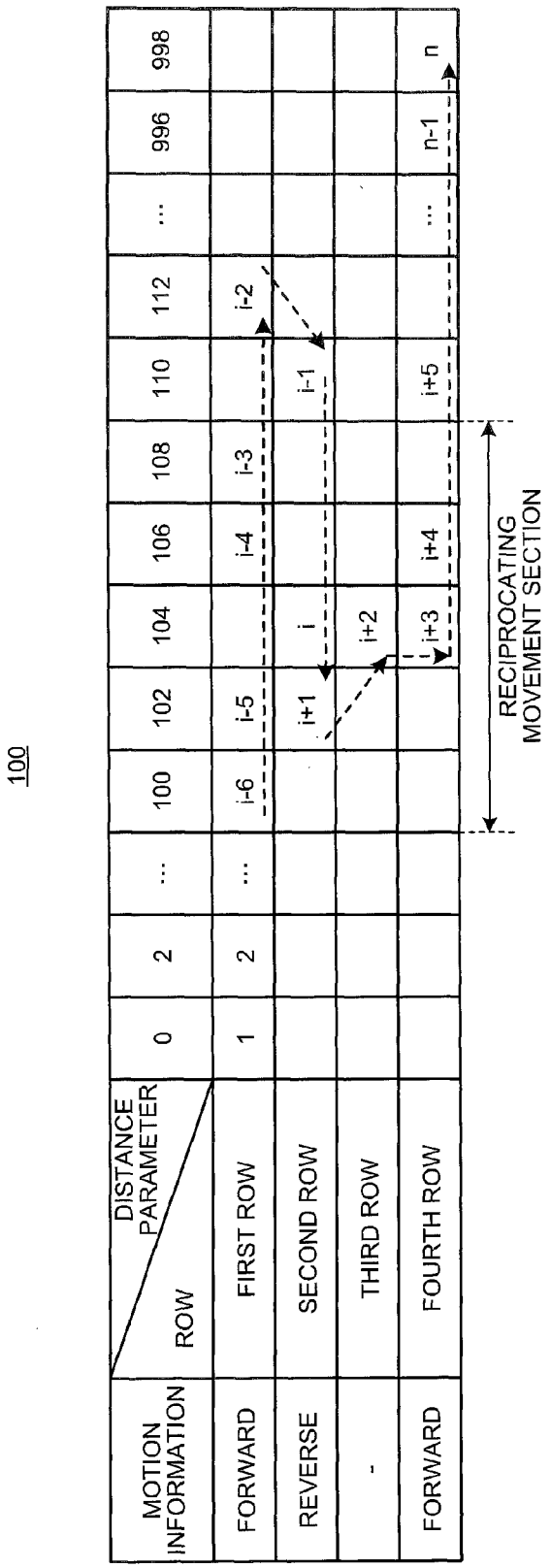
FIG. 4 is a schematic diagram illustrating an example of a position series index created by an index creation unit illustrated in FIG. 1.

The index creation unit 533 creates a position series index that represents a relationship between an imaging sequence of a series of images acquired by the capsule endoscope 2 and the capsule position. FIG. 4 is a schematic diagram illustrating an example of the position series index. The position series index 100 is a two-dimensional array table in which image numbers that represent the imaging sequence of images are arranged according to a distance from a predetermined reference position to the capsule position. As an example, the position of the mouth of the subject 10 from which the capsule endoscope 2 is swallowed is set as the reference position.

The numerical values written in the uppermost row of the position series index 100 illustrated in FIG. 4 are parameters representing a distance from the reference position. Hereinafter, the parameter that represents a distance from the reference position is simply referred to as a distance parameter. In the first embodiment, a distance (cm) from the reference position is defined as the distance parameter. The numerical values written in the second and lower rows of the position series index 100 are the image numbers, and each image number is written in a column of a distance parameter corresponding to the capsule position of the image. For example, it is indicated that the image of the image number (i−6) is an image captured at a position corresponding to a distance parameter 100. A distance between the capsule positions of the images of the image number (i−6) and (i−5) written in fields adjacent to each other is 2 cm, and a distance between the capsule positions of the images of the image number (i−5) and (i−4) written in fields adjacent to each other with one field in between is 4 cm. How to create the position series index 100 will be described later. Hereinafter, an image to which an image number i is attached is also referred to as an image (i).

When a selection signal to select one of a series of images is inputted to the image identification unit 534 from the input unit 51 according to a user operation to the input unit 51, the image identification unit 534 identifies image data corresponding to the selection signal as identified image data. Hereinafter, an image corresponding to the identified image data, that is, an image selected by the user, is referred to as an identified image.

The determination unit 535 determines whether or not the identified image that is identified by the image identification unit 534 is an image acquired in a section where the capsule endoscope 2 makes a reciprocating movement in which the capsule endoscope 2 moves forward and backward in the subject based on the position series index 100 illustrated in FIG. 4.

In more detail, the determination unit 535 includes an identification unit 535*a* that identifies a plurality of images where the capsule position or an imaging time is within a predetermined range with respect to the identified image. The determination unit 535 determines that the identified image is an image acquired in a section where the capsule endoscope 2 makes the reciprocating movement when the plurality of images identified by the identification unit 535*a* include two or more image groups which continue in a forward direction in time series as well as continue in a forward direction in position series.

When the determination unit 535 determines that the identified image is an image acquired during the reciprocating movement of the capsule endoscope 2, the candidate image extraction unit 536 extracts an image that is more appropriate as an image to set a feature point from among images acquired during the reciprocating movement. Hereinafter, the image extracted by the candidate image extraction unit 536 is referred to as a candidate image.

The feature point setting unit 537 sets the identified image that is identified by the image identification unit 534 or the candidate image that is extracted by the candidate image extraction unit 536 as an image that indicates a feature point and sets a capsule position of the image that indicates the feature point as a feature point according to a signal inputted from the input unit 51. Hereinafter, the image that indicates the feature point is referred to as a feature point image.

The display control unit 538 causes the display unit 55 to display a series of images in a predetermined format and causes the display unit 55 to display the candidate image extracted by the candidate image extraction unit 536 in a predetermined format based on display image data that is image-processed by the image processing unit 531.

The storage unit 54 is realized by a semiconductor memory such as a flash memory, a RAM, and a ROM, a recording medium such as an HDD, an MO, a CD-R, and a DVD-R, a writing/reading device that writes and reads information to and from the recording medium, and the like. The storage unit 54 includes an image data storage unit 541 that stores the display image data that is image-processed by the image processing unit 531 and stores the capsule position of each image in association with the image data, an index storage unit 542 that stores the position series index created by the index creation unit 533, a feature point storage unit 543 that stores information related to the feature point image, a setting condition storage unit 544 that stores a condition used when extracting a candidate image, and a program storage unit 545 that stores a program and various information to operate the image display device 5 and cause various functions to be performed.

Among them, the setting condition storage unit 544 stores a setting condition of a section where the capsule endoscope 2 makes the reciprocating movement in the subject 10 and a condition when extracting a candidate image from a section where the capsule endoscope 2 makes the reciprocating movement. Hereinafter, the section where the capsule endoscope 2 makes the reciprocating movement is simply referred to as a reciprocating movement section. The setting condition of the reciprocating movement section includes conditions such as the length of the reciprocating movement section, in other words, the distance of the reciprocating movement section, the number of images acquired in the reciprocating movement section or the time required to move in the reciprocating movement section, and the position of the reciprocating movement section with respect to the identified image. As an extraction condition of the candidate image, there is a condition that an image captured when the capsule endoscope 2 passes through the reciprocating movement section for the first time is defined as the candidate image or a condition that an image captured when the capsule endoscope 2 passes through the reciprocating movement section for the last time is defined as the candidate image. The setting condition storage unit 544 stores a predetermined initial condition in advance as the setting condition of the reciprocating movement section and the extraction condition of the candidate image. However, a user may overwrite a setting condition of the reciprocating movement section and an extraction condition of the candidate image which the user desires by an operation using the input unit 51.

The display unit 55 is realized by a display device such as a CRT display, a liquid crystal display, and an EL display. The display unit 55 displays a series of images, the candidate image extracted by the candidate image extraction unit 536, the other related information, and the like on a screen in a predetermined format under control of the display control unit 538.

Figure 5:
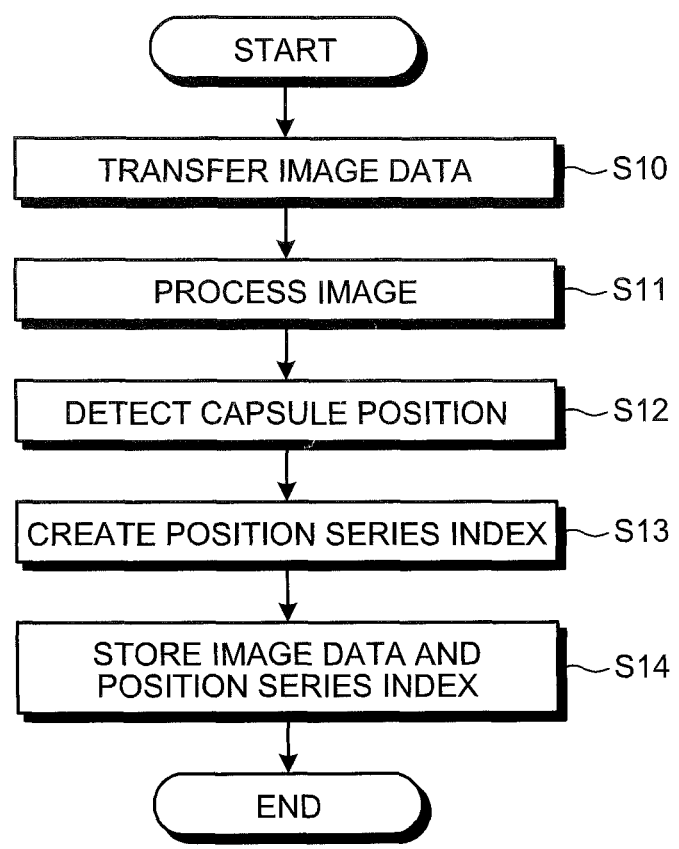
FIG. 5 is a flowchart illustrating processing that transfers image data from the receiving device illustrated in FIG. 1 to the image display device.

Next, an operation of the image display device 5 will be described. FIG. 5 is a flowchart illustrating processing that transfers (downloads) image data acquired by examination using the capsule endoscope 2 from the receiving device 3 to the image display device 5.

First, in step S10, the receiving device 3 is set to the cradle 3*a* connected to the image display device 5 (see FIG. 1), and thereby the image data is transferred from the receiving device 3 to the image display device 5. Alternatively, the image data may be transferred from the receiving device 3 to the image display device 5 through various communication lines.

In the following step S11, the image processing unit 531 creates display image data by performing image processing such as white balance processing, demosaicing, color conversion, density conversion, smoothing, and sharpening on each image corresponding to the image data transferred from the receiving device 3. In this case, the image processing unit 531 may perform image processing such as calculation of average color of each image along with the image processing described above.

In the following step S12, the position information acquisition unit 532 detects the capsule position of each image based on the reception intensity information in the related information of the image data.

In the following step S13, the index creation unit 533 creates the position series index based on the capsule positions of a series of images detected in step S12. Specifically, as illustrated in FIG. 4, the image numbers of a series of images are sequentially inputted into columns of distance parameter corresponding to the capsule position of the image in ascending order. In this case, when the distance parameter is the same as that of the previous image number or the distance parameter with respect to the previous image number changes, for example, from increase to decrease or decrease to increase, a row of the position series index 100 is added and thereafter the image numbers are inputted into the added row.

For example, in FIG. 4, when inputting the image number (i−1), while the distance parameter (112) of the previous image number (i−2) is increased from the distance parameter (108) of the further previous image number (i−3), the distance parameter (110) of the image number (i−1) is decreased from the distance parameter (112) of the image number (i−2). In this case, the image number (i−1) and the following image numbers are inputted to an added row (second row). When inputting the image number (i+2), while the distance parameter (102) of the previous image number (i+1) is decreased from the distance parameter (104) of the further previous image number (i), the distance parameter (104) of the image number (i+2) is increased from the distance parameter (102) of the image number (i+1). In this case, the image number (i+2) and the following image numbers are inputted to an added row (third row). Further, the distance parameter (104) of the image number (i+3) is the same as the distance parameter of the previous image number (i+2), so that the image number (i+3) and the following image numbers are inputted to an added row (fourth row).

In the following step S14, the storage unit 54 stores the image data on which image processing is performed in step S11, stores the capsule positions detected in step S12 in association with the image data, and further, stores the position series index created in step S13. Thereby, the transfer processing of the image data from the receiving device 3 to the image display device 5 is completed.

Figure 6:
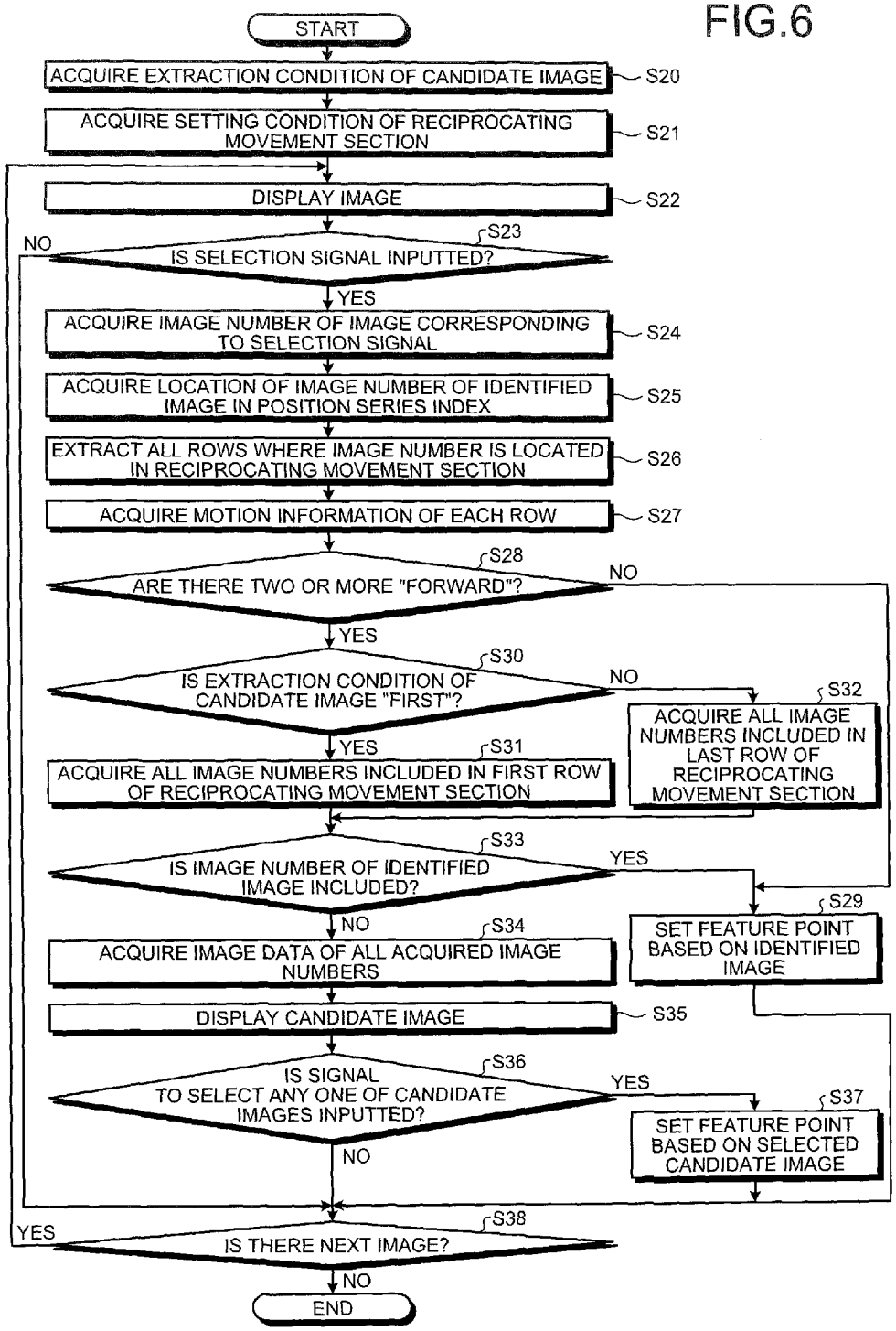
FIG. 6 is a flowchart illustrating feature point setting processing performed by the image display device illustrated in FIG. 1.

Next, feature point setting processing on a series of images will be described. FIG. 6 is a flowchart illustrating the feature point setting processing performed by the image display device 5. In the description below, it is assumed that the position series index illustrated in FIG. 4 is created and the position series index is stored in the storage unit 54.

First, in step S20, the control unit 53 acquires the extraction condition of the candidate image from the setting condition storage unit 544. Specifically, the control unit 53 acquires either of the following conditions: extracting an image when the capsule endoscope 2 "first" passes through as the candidate image and extracting an image when the capsule endoscope 2 "last" passes through as the candidate image from the section where the capsule endoscope 2 makes the reciprocating movement.

In the following step S21, the control unit 53 acquires the setting condition of the reciprocating movement section from the setting condition storage unit 544. In the first embodiment, a case will be described in which the reciprocating movement section is a range where the capsule position is ±Δ from the center which is the identified image. In FIG. 4, as an example, is 4 cm.

In the following step S22, the control unit 53 reads the image data from the image data storage unit 541 and causes the display unit 55 to sequentially display a series of images acquired by the capsule endoscope 2 in a predetermined format based on the image data.

Figure 7:
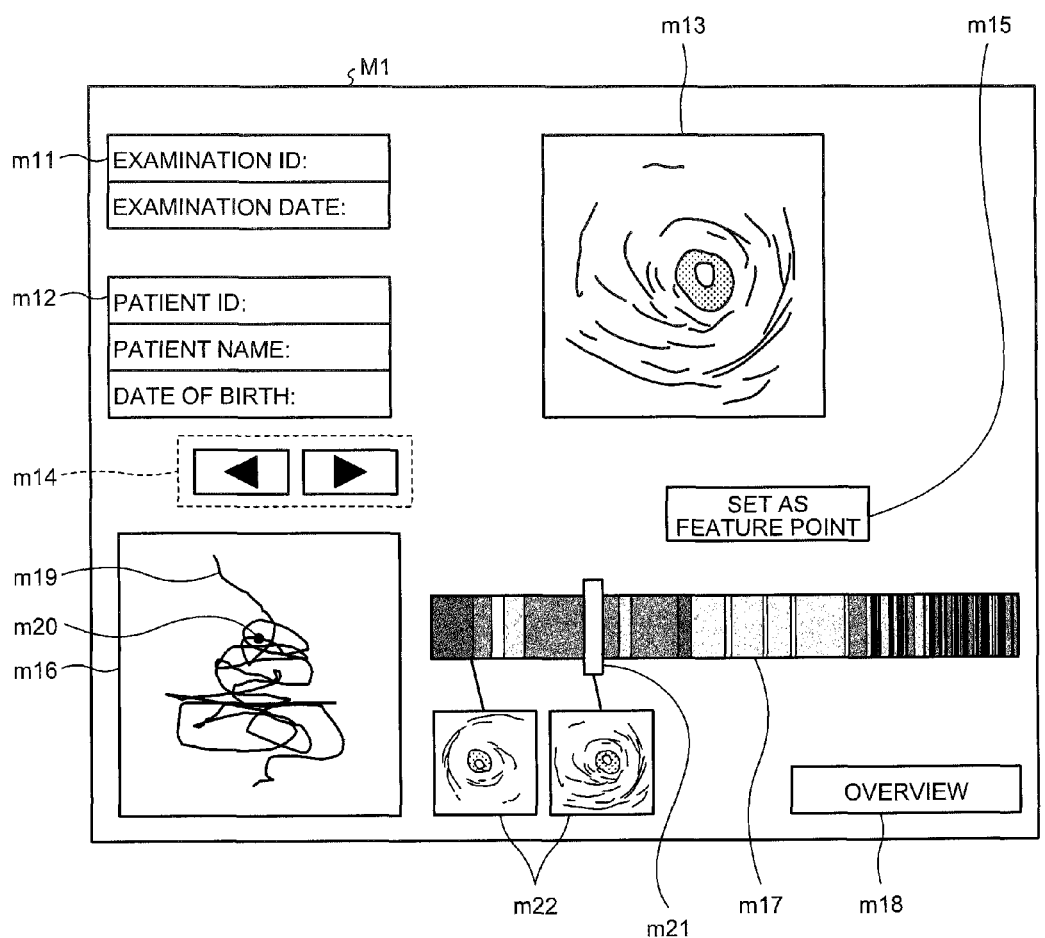
FIG. 7 is a schematic diagram illustrating a display example of a series of images acquired by the capsule endoscope illustrated in FIG. 1.

FIG. 7 is a schematic diagram illustrating a display example of the series of images acquired by the capsule endoscope 2. A display screen M1 illustrated in FIG. 7 includes an examination information display field m11 in which examination information such as examination ID and examination date is displayed, a patient information display field m12 in which patient information such as patient ID, patient name, and date of birth is displayed, a main display area m13 in which a series of images are sequentially displayed in a pseudo moving image format, an operation button group m14 used for operation of a reproduction operation of the images displayed in the main display area m13, a feature point setting button m15 used to input an instruction to select an image being displayed in the main display area m13 as a feature point image, a track display area m16 in which a track of the capsule endoscope 2 in the subject is displayed, an average color bar m17, and an overview button m18 used to input an instruction to switch a display format of the series of images from the pseudo moving image format to a still image list display format. When a plurality of imaging units 21 are provided to the capsule endoscope 2 (see FIG. 2) and the imaging can be performed in a plurality of directions, a plurality of main display areas m13 may be provided corresponding to these imaging units 21.

The feature point setting button m15 is used to select an image that includes a portion which a user wants to set as a feature point. When a predetermined pointer operation such as, a click is performed on the feature point setting button m15 by using the input unit 51, a selection signal to select an image displayed in the main display area m13 at this timing as a feature point image is inputted from the input unit 51 to the control unit 53.

In the track display area m16, a track m19 where the capsule positions associated with images acquired by the position information acquisition unit 532 are connected and a marker m20 that indicates the capsule position corresponding to the image being displayed in the main display area m13 are displayed. The user can roughly know the capsule position of the image being displayed in the main display area m13 by referring to the position of the marker m20 on the track m19.

The average color bar m17 is a bar in which average colors calculated by the image processing unit 531 for each image are arranged in a band-like area in the arrangement order of the images, that is, in the order of the time of imaging. The average color bar m17 is provided with a slider m21 that indicates a position corresponding to the image being displayed in the main display area m13. The user can roughly know the position in the subject of the image being displayed in the main display area m13 by referring to the position of the slider m21 in the average color bar m17. It is possible to change the image displayed in the main display area m13 by moving the slider m21 along the average color bar m17 by a predetermined pointer operation using the input unit 51.

Reduced images m22 that are obtained by reducing the feature point images are displayed as thumbnails below the average color bar m17. Each reduced image m22 is connected by a line to a corresponding position on the average color bar m17.

In the following step S23, the control unit 53 determines whether or not the selection signal to select the image being displayed in the main display area m13 as a feature point image is inputted from the input unit 51. When the selection signal of the image is not inputted (step S23: No), the processing proceeds to step S38 described later.

On the other hand, when the selection signal of the image is inputted (step S23: Yes), the image identification unit 534 acquires the image number of the image corresponding to the selection signal (that is, the identified image) (step S24).

In the following step S25, the determination unit 535 reads the position series index from the index storage unit 542 and acquires the location of the image number of the identified image in the position series index. For example, when the image number of the identified image is i, the image number i in the position series index 100 illustrated in FIG. 4 is located in the second row of the column of the distance parameter (104).

In the following step S26, the determination unit 535 sets a reciprocating movement section for the identified image and extracts all rows where an image number is located in the reciprocating movement section. For example, as illustrated in FIG. 4, when a range where the capsule position is ±4 cm from the center, which is the identified image i, is defined as the reciprocating movement section, a section from the column of distance parameter (100) to the column of distance parameter (108) is defined as the reciprocating movement section. In this case, the determination unit 535 extracts the first to the fourth rows, where there is an image number in the above reciprocating movement section, from the position series index.

In the following step S27, the determination unit 535 acquires motion information of the capsule endoscope 2 in each row extracted in step S26. Here, the motion information is information that indicates a reciprocating motion in which the capsule endoscope 2 moves forward and reverse when the images corresponding to the image numbers written in each row are acquired. The motion information includes "forward" that indicates a movement in the forward direction, that is, a direction from mouth to anus, "reverse" that indicates a movement in the reverse direction, that is, a direction from anus to mouth, and "staying" that is neither the "forward" nor the "reverse". In FIG. 4, the staying is described by a code "−". The motion information can be discriminated by the image numbers written in each row and the distance parameters. Specifically, when continuous image numbers are arranged in ascending order corresponding to the forward direction for each row of the position series index, if the distance parameter corresponding to each image number increases, the motion information of the row is "forward". On the other hand, when continuous image numbers are arranged in ascending order corresponding to the forward direction, if the distance parameter corresponding to each image number decreases, the motion information of the row is "reverse". When only one image number is inputted in one row, the motion information is the staying "−".

Specifically, in the case of FIG. 4, it is determined that the motion information of the first row that includes the image numbers (i−6) to (i−3) is "forward", the motion information of the second row that includes the image numbers (i) and (i+1) is "reverse", the motion information of the third row that includes the image number (i+2) is the staying, and the motion information of the fourth row that includes the image numbers (i+3) and (i+4) is "forward". Thereby, it is possible to know the motion of the capsule endoscope 2 when the images corresponding to the image numbers inputted into each row are acquired.

In the following step S28, the determination unit 535 determines whether or not the motion information acquired in step S27 includes two or more "forward". For example, in the reciprocating movement section illustrated in FIG. 4, the motion information of the first and the fourth rows is "forward", so that there are two or more "forward".

When there are not two or more "forward" (step S28: No), it is considered that the capsule endoscope 2 proceeds only in the forward direction in the reciprocating movement section. Therefore, in this case, the feature point setting unit 537 sets a feature point based on the identified image, that is, the image selected by the user (step S29). Specifically, the feature point setting unit 537 adds a flag indicating that the identified image is a feature point image to the identified image and sets the capsule position of the feature point image as the feature point. Thereafter, the processing proceeds to step S38 described later.

On the other hand, when there are two or more "forward" (step S28: Yes), it is considered that the capsule endoscope 2 makes a reciprocating movement or temporarily stays at the same position in the reciprocating movement section. In this case, there may be another image of the same portion as that of the identified image or a portion close to the portion of the identified image. Therefore, the candidate image extraction unit 536 extracts an image more appropriate as the feature point image as a candidate image.

In step S30, the candidate image extraction unit 536 determines whether or not the extraction condition of the candidate image acquired in step S20 is an image when the capsule endoscope 2 "first" passes through the section where the capsule endoscope 2 makes a reciprocating movement.

When the extraction condition of the candidate image is the "first" (step S30: Yes), the candidate image extraction unit 536 acquires all the image numbers included in a first row of the reciprocating movement section, that is, all the image numbers included in a first forward path (step S31). On the other hand, when the extraction condition of the candidate image is not the "first" (step S30: No), that is, when the extraction condition of the candidate image is the "last", the candidate image extraction unit 536 acquires all the image numbers included in a last row of the reciprocating movement section, that is, all the image numbers included in a last forward path (step S32).

In the following step S33, the candidate image extraction unit 536 determines whether or not the image number of the identified image, that is, the image number corresponding to the selection signal inputted in step S23, is included in the image numbers acquired in step S31 or S32.

When the image number of the identified image is included in the image numbers acquired in step S31 or S32 (step S33: Yes), the processing proceeds to step S29.

On the other hand, when the image number of the identified image is not included in the image numbers acquired in step S31 or S32 (step S33: No), the candidate image extraction unit 536 acquires image data corresponding to all the image numbers acquired in step S31 or S32 from the image data storage unit 541 (step S34).

In the following step S35, the display control unit 538 causes the display unit 55 to display an image corresponding to the image data acquired by the candidate image extraction unit 536 in step S34 as a candidate image.

Figure 8:
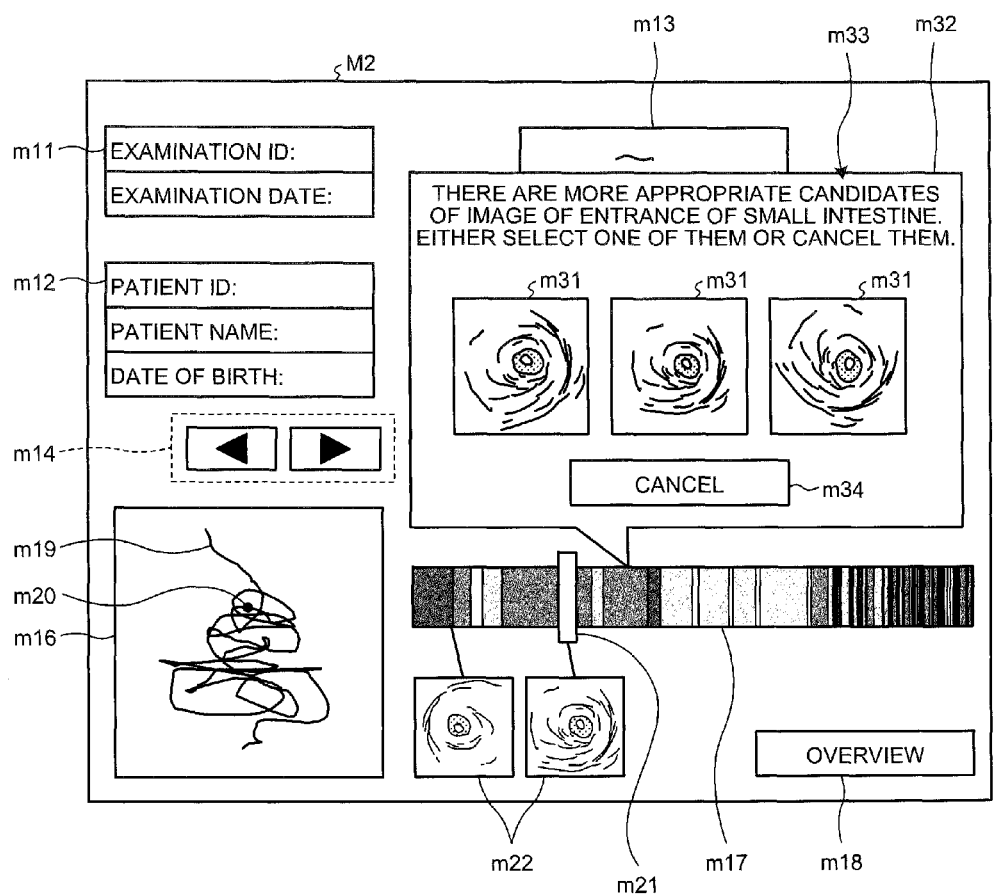
FIG. 8 is a schematic diagram illustrating a display example of a candidate image.

FIG. 8 is a schematic diagram illustrating a display example of the candidate image. In a display screen M2 illustrated in FIG. 8, a window m32 including a plurality of candidate images m31 is superimposed on the display screen M1 illustrated in FIG. 7 and displayed. In the window m32, a message display field m33 for a user and a cancel button m34 are also displayed. In the message display field m33, a message urging the user to select a feature point image from among the candidate images m31 is displayed. When a predetermined pointer operation such as, a click is performed on any one of the candidate images m31 displayed in the window m32 by using the input unit 51, a signal to select the candidate image on which the pointer operation is performed is inputted from the input unit 51 to the control unit 53. When a predetermined pointer operation such as, a click is performed on the cancel button m34 by using the input unit 51, a signal that instructs cancellation of the setting of feature point is inputted from the input unit 51 to the control unit 53.

In step S36, the feature point setting unit 537 determines whether or not a signal to select any one of the candidate images m31 displayed in the window m32 is inputted from the input unit 51. When the signal to select any one of the candidate images m31 is inputted (step S36: Yes), the feature point setting unit 537 sets a feature point based on the selected candidate image (step S37). Specifically, the feature point setting unit 537 adds a flag indicating that the selected candidate image is a feature point image to the selected candidate image and sets the capsule position of the feature point image as the feature point.

On the other hand, when the signal to select any one of the candidate images m31 is not inputted (step S36: No), that is, when a signal that instructs cancellation of the setting of the feature point is inputted, the processing proceeds to step S38.

In step S38, the control unit 53 determines whether or not there is an image to be displayed next. When there is an image to be displayed next (step S38: Yes), the processing returns to step S22. On the other hand, when there is no image to be displayed next (step S38: No), a series of processing ends.

As described above, according to the first embodiment of the present invention, when an image acquired while the capsule endoscope 2 makes a reciprocating movement is selected as a feature point image by a user operation, if there is an image more appropriate as the feature point image in a series of images, the image is displayed on a screen as a candidate image, so that the user can set a more appropriate feature point by referring to the candidate image displayed on the screen.

Further, according to the first embodiment of the present invention, it is possible to correctly extract a section, where the capsule endoscope 2 makes a reciprocating movement, with simple processing by using the image numbers that indicate an arrangement order of the images and the distance parameters that represent the capsule positions of the images.

Modified Example 1

Figure 9:
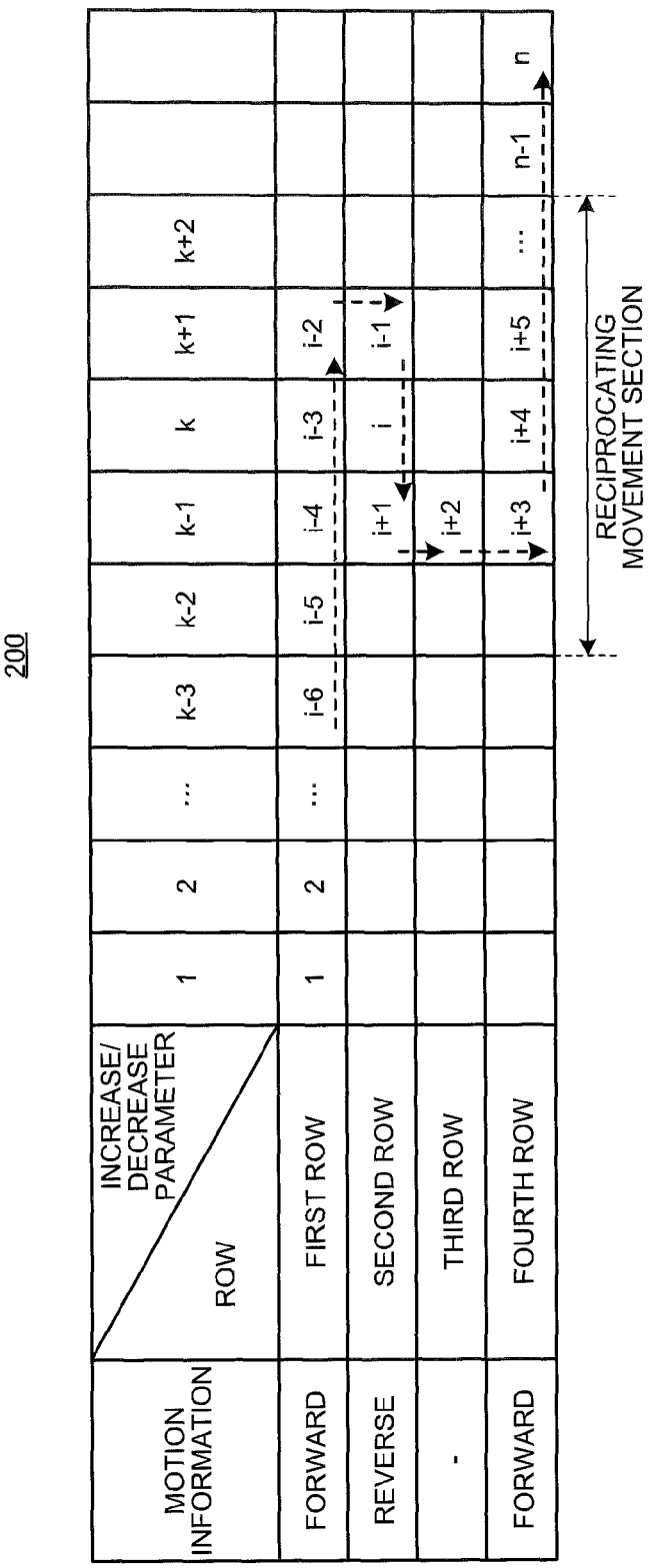
FIG. 9 is a schematic diagram illustrating an example of an image number index.

Next, a modified example 1 of the first embodiment of the present invention will be described. FIG. 9 is a schematic diagram illustrating another example of an index used when determining motion information of the capsule endoscope 2. An image number index 200 illustrated in FIG. 9 is a two-dimensional array table in which the image numbers that represent an imaging sequence of images are arrayed based on the increase/decrease of distance from a predetermined reference position to the capsule position of an image. The numerical values written in the uppermost row of the image number index 200 are parameters representing the increase/decrease of distance from the reference position to the capsule position. Hereinafter, the parameter that represents the increase/decrease of distance from the reference position to the capsule position is simply referred to as an increase/decrease parameter. The numerical values written in the second and lower rows of the image number index 200 are the image numbers. It is indicated that, among the image numbers written in the same row, the greater the value of the increase/decrease parameter, the longer the distance from the reference position to the capsule position.

In the image number index 200, a row is added when the distance from the reference position to the capsule position is the same as that in the previous image, is changed from increase to decrease, or is changed from decrease to increase. For example, the image number (i−1) is inputted into a newly added row because the distance that has been increasing begins to decrease. Further, the image number (i+2) is inputted into a newly added row because the distance that has been decreasing begins to increase. Further, the image number (i+3) is inputted into a newly added row because the distance is the same as that of the previous image number (i+2). In each row, a continuous image number is inputted in an adjacent field regardless of an absolute value of the distance from the reference position to the capsule position.

In the case of such an image number index 200, for example, the reciprocating movement section is set in a form of ±Δ columns based on the kth column that includes the image number i of the identified image. In FIG. 9, k±2 columns are defined as the reciprocating movement section. Based on the reciprocating movement section set in this way, it is possible to determine the motion information of each row and extract a candidate image in the same manner as in the first embodiment.

Modified Example 2

Next, a modified example 2 of the first embodiment of the present invention will be described. FIG. 10 is a schematic diagram illustrating further another example of the index used when determining the motion information of the capsule endoscope 2. A time series index 300 illustrated in FIG. 10 is a two-dimensional array table in which an imaging distance that represents a distance from a predetermined reference position to the capsule position of each image is arrayed according to an imaging time period that represents an elapsed time from an imaging start time to an imaging time of the image. Here, when an imaging frame rate is constant, the imaging time period corresponds to the imaging sequence, so that the image number that represents the imaging sequence of each image can be used as a time parameter that represents the imaging time period.

In the time series index 300, a row is added when the imaging distance (cm) is the same as that of the most previously imaged image, is changed from increase to decrease, or is changed from decrease to increase. For example, the imaging distance 110 cm corresponding to the time parameter (i−1) is inputted into a newly added row because the imaging distance that has been increasing begins to decrease. The imaging distance 104 cm corresponding to the time parameter (i+2) is inputted into a newly added row because the imaging distance that has been decreasing begins to increase. Further, the imaging distance 104 cm corresponding to the time parameter (i+3) is inputted into a newly added row because the imaging distance is not changed from that of the previous image number (i+2).

In the case of such a time series index 300, for example, the reciprocating movement section is set in a form of ±Δ based on the time parameter i of the identified image. In FIG. 10, i±4 is defined as the reciprocating movement section. By setting the reciprocating movement section in this way, it is possible to determine the motion information of each row and extract a candidate image in the same manner as in the first embodiment.

Modified Example 3

Next, a modified example 3 of the first embodiment of the present invention will be described. In the first embodiment described above, the position series index is created when the image data is transferred from the receiving device 3 to the image display device 5. However, the position series index may be created at any time before the feature point setting processing is performed. For example, the position series index may be created when a user sets the feature point or a user opens an image data file to observe an image. The same goes for a case in which the image number index 200 described in the modified example 1 or the time series index 300 described in the modified example 2 is created instead of the position series index.

Second Embodiment

Next, a second embodiment of the present invention will be described. In the first embodiment described above, by determining whether or not two or more rows where the motion information is "forward" are included in the reciprocating movement section with respect to the identified image selected by a user operation, it is determined whether or not the capsule endoscope 2 makes a reciprocating movement or is staying in the reciprocating movement section. However, the movement of the capsule endoscope 2 may be directly determined from the reciprocating movement section without individually determining the motion information of each row.

Figure 11:
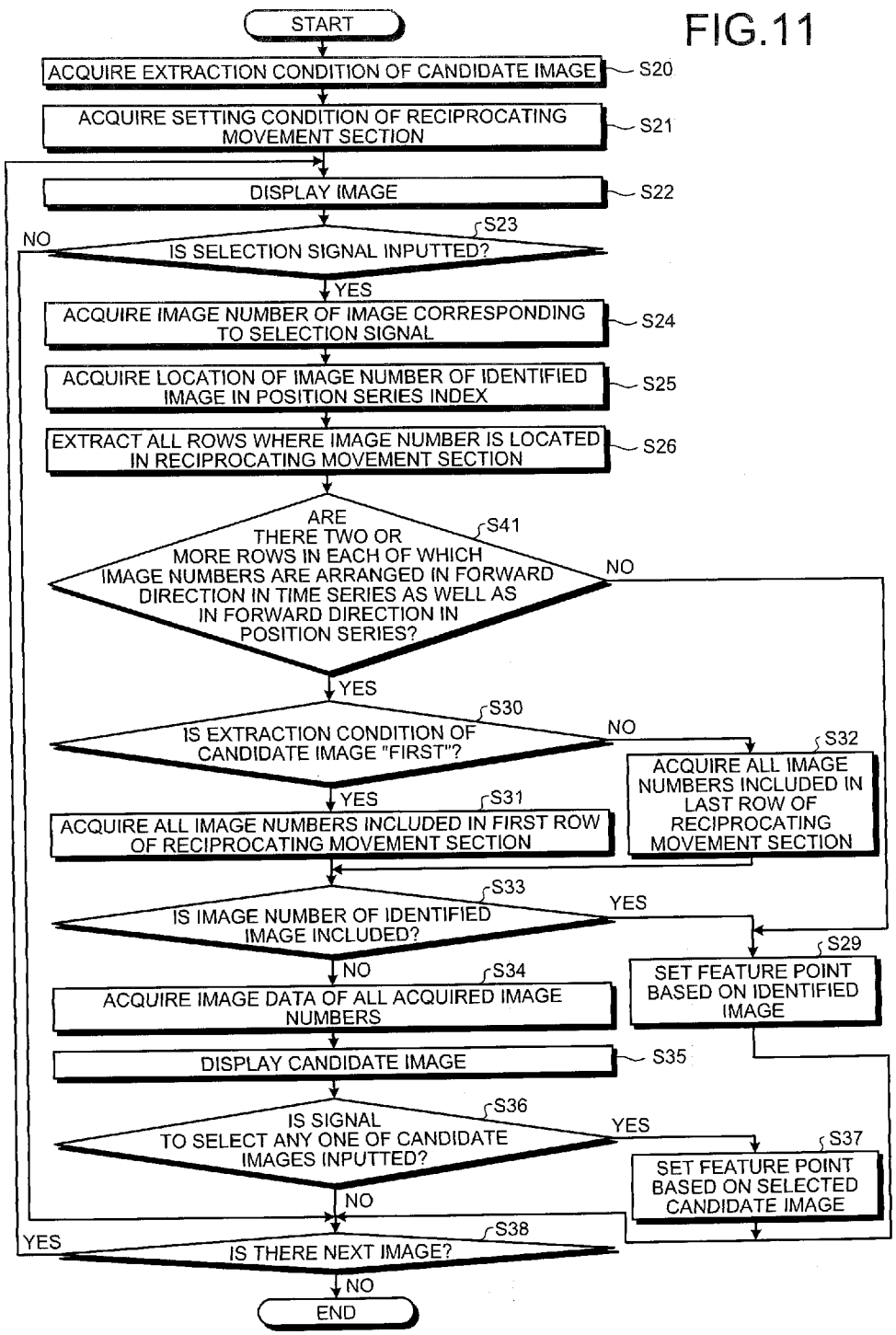
FIG. 11 is a flowchart illustrating feature point setting processing performed by an image display device according to a second embodiment of the present invention.

FIG. 11 is a flowchart illustrating feature point setting processing performed by an image display device according to the second embodiment of the present invention. A configuration of the entire capsule endoscope system and a configuration of the image display device of the second embodiment are the same as those of the first embodiment illustrated in FIGS. 1 to 3. Steps S20 to S26 illustrated in FIG. 11 are the same as those in the first embodiment.

In step S41 following step S26, the determination unit 535 determines whether or not the images included in the reciprocating movement section include two or more rows, that is, two or more image number groups, in each of which the image numbers are arranged in the forward direction in time series, that is, in ascending order, and the image numbers are arranged in the forward direction in position series.

When the reciprocating movement section does not include two or more rows, in each of which the image numbers are arranged in the forward direction in time series as well as in the forward direction in position series (step S41: No), the processing proceeds to step S29. On the other hand, when the reciprocating movement section includes two or more rows, in each of which the image numbers are arranged in the forward direction in time series as well as in the forward direction in position series (step S41: Yes), the processing proceeds to step S30. The processing of steps S29 to S38 are the same as those in the first embodiment.

As described above, according to the second embodiment of the present invention, it is determined whether or not the capsule endoscope 2 makes a reciprocating movement in a reciprocating movement section based on the arrangement order of the image numbers included in the reciprocating movement section instead of determining the motion information for each row of the position series index 100, so that it is possible to simplify the processing.

Also in a case in which the image number index 200 described in the modified example 1 or the time series index 300 described in the modified example 2 is created instead of the position series index, it is possible to determine the motion of the capsule endoscope 2 by the same processing.

Third Embodiment

Figure 12:
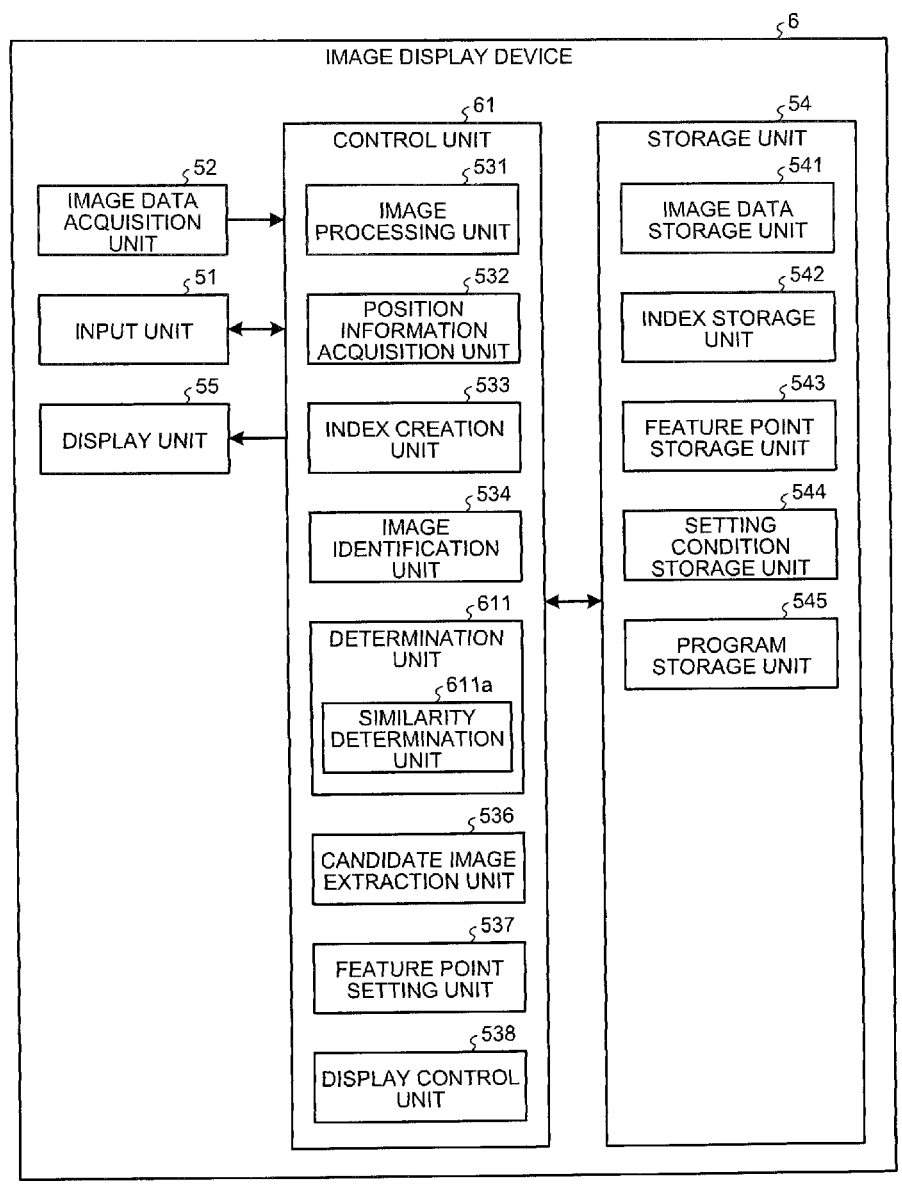
FIG. 12 is a block diagram illustrating a configuration of an image display device according to a third embodiment of the present invention.

Next, a third embodiment of the present invention will be described. A capsule endoscope system according to the third embodiment of the present invention includes an image display device 6 illustrated in FIG. 12 instead of the image display device 5 illustrated in FIG. 1. FIG. 12 is a block diagram illustrating a configuration of the image display device according to the third embodiment of the present invention. The image display device 6 illustrated in FIG. 12 includes a control unit 61 instead of the control unit 53 illustrated in FIG. 3. A configuration and an operation of each unit in the image display device 6 other than the control unit 61 and a configuration of the entire capsule endoscope system are the same as those of the first embodiment illustrated in FIGS. 1 and 2.

The control unit 61 includes a determination unit 611 instead of the determination unit 535 included in the control unit 53 illustrated in FIG. 3. The determination unit 611 includes a similarity determination unit 611a that determines a similarity between each of a plurality of images where the capsule position or the imaging time is within a predetermined range with respect to an identified image identified by the image identification unit 534 and the identified image. When two or more image groups which include an image that is determined to be similar to the identified image by the similarity determination unit 611a and in which the image numbers are continuous are included in the plurality of images, the determination unit 611 determines that the identified image is an image acquired in a section where the capsule endoscope 2 makes a reciprocating movement. A configuration and an operation of each unit in the control unit 61 other than the determination unit 611 are the same as those in the first embodiment.

Figure 13:
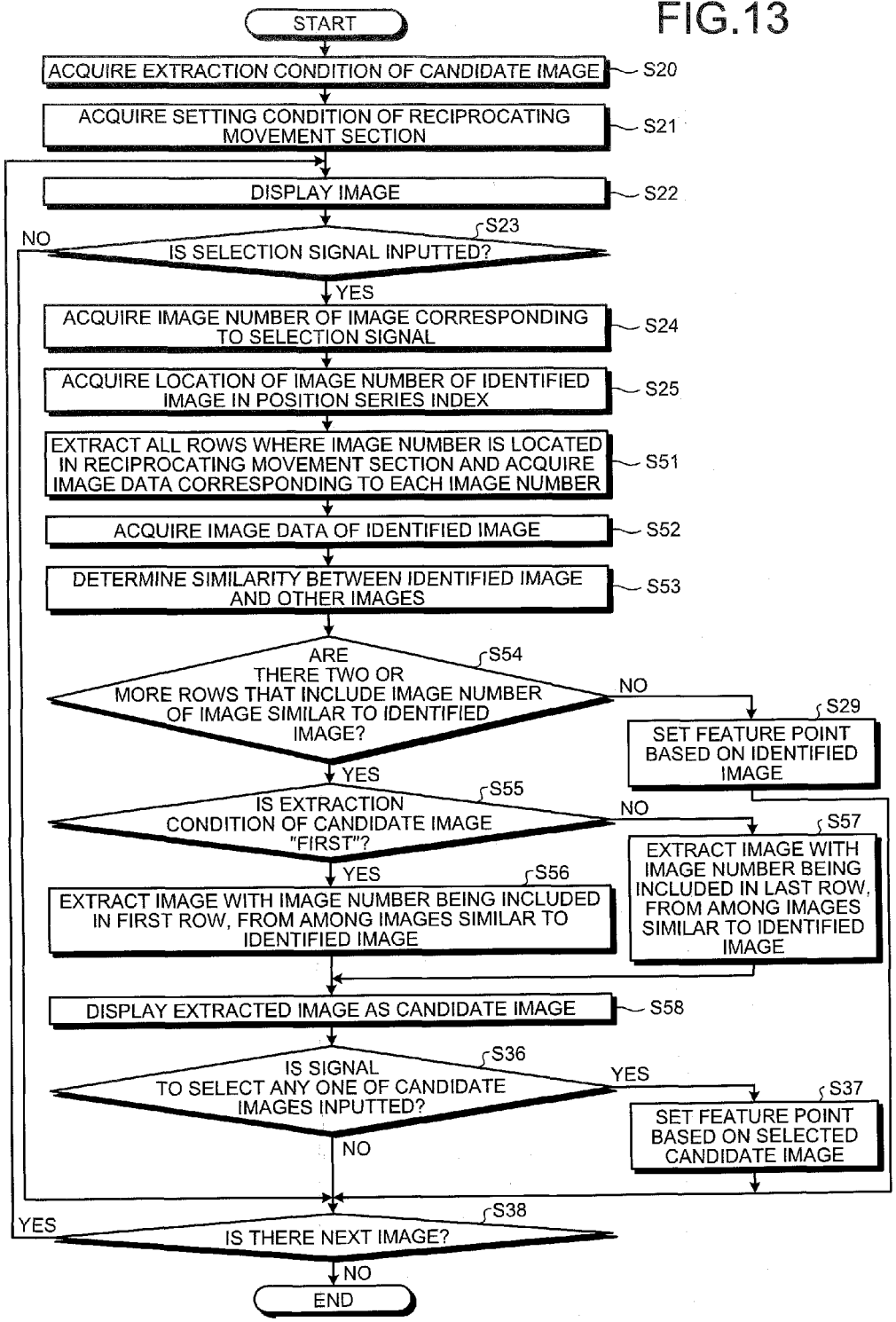
FIG. 13 is a flowchart illustrating feature point setting processing performed by an image display device according to the third embodiment of the present invention.

FIG. 13 is a flowchart illustrating the feature point setting processing performed by the image display device 6. Steps S20 to S25 illustrated in FIG. 13 are the same as those in the first embodiment.

In step S51 following step S25, the determination unit 611 sets a reciprocating movement section for the identified image, extracts all rows where an image number is located in the reciprocating movement section, and acquires image data corresponding to each image number from the image data storage unit 541.

In the following step S52, the determination unit 611 acquires image data of the identified image.

In the following step S53, the similarity determination unit 611a determines a similarity between the identified image and the other images based on the image data acquired in step S51 and S52. As a method for determining the similarity, various known methods can be applied. Specifically, Normalized Cross-Correlation (NCC), SSD (Sum of Squared Difference), and SAD (Sum of Absolute Difference) by template matching and the like are used as an index representing the similarity. It is indicated that the greater the value of NCC is, the higher the similarity between the images is, and the smaller the value of SSD and SAD is, the higher the similarity between the images is. Therefore, an image where the NCC is greater than or equal to a predetermined value and an image where the SSD or the SAD is smaller than or equal to a predetermined value are determined to be similar to the identified image.

In the following step S54, the determination unit 611 determines whether or not there are two or more rows that include one or more image numbers of images similar to the identified image. In other words, it is determined whether or not there are two or more image groups which include an image similar to the identified image and in which the image numbers are continuous.

When there are not two or more rows that include an image number of an image similar to the identified image (step S54: No), the feature point setting unit 537 sets a feature point based on the identified image (the image corresponding to the selection signal inputted in step S23) (step S29). Thereafter, the processing proceeds to step S38 described later.

On the other hand, when there are two or more rows that include an image number of an image similar to the identified image (step S54: Yes), the candidate image extraction unit 536 determines whether or not the extraction condition of the candidate image acquired in step S20 is an image when the capsule endoscope 2 "first" passes through the section where the capsule endoscope 2 makes a reciprocating movement (step S55).

When the extraction condition of the candidate image is the "first" (step S55: Yes), the candidate image extraction unit 536 extracts an image with an image number which is included in the first row of the reciprocating movement section, that is, the first forward path, from among the images similar to the identified image (step S56). On the other hand, when the extraction condition of the candidate image is not the "first" (step S55: No), the candidate image extraction unit 536 extracts an image with an image number which is included in the last row of the reciprocating movement section, that is, the last forward path, from among the images similar to the identified image (step S57).

In the following step S58, the candidate image extraction unit 536 causes the display unit 55 to display the image extracted in step S56 or S57 as a candidate image. The following steps S36 to S38 are the same as those in the first embodiment described with reference to FIG. 6.

As described above, according to the third embodiment of the present invention, the candidate image is extracted based on the determination result of the similarity with the identified image, so that it is possible to present a more appropriate candidate image to a user.

Fourth Embodiment

Figure 14:
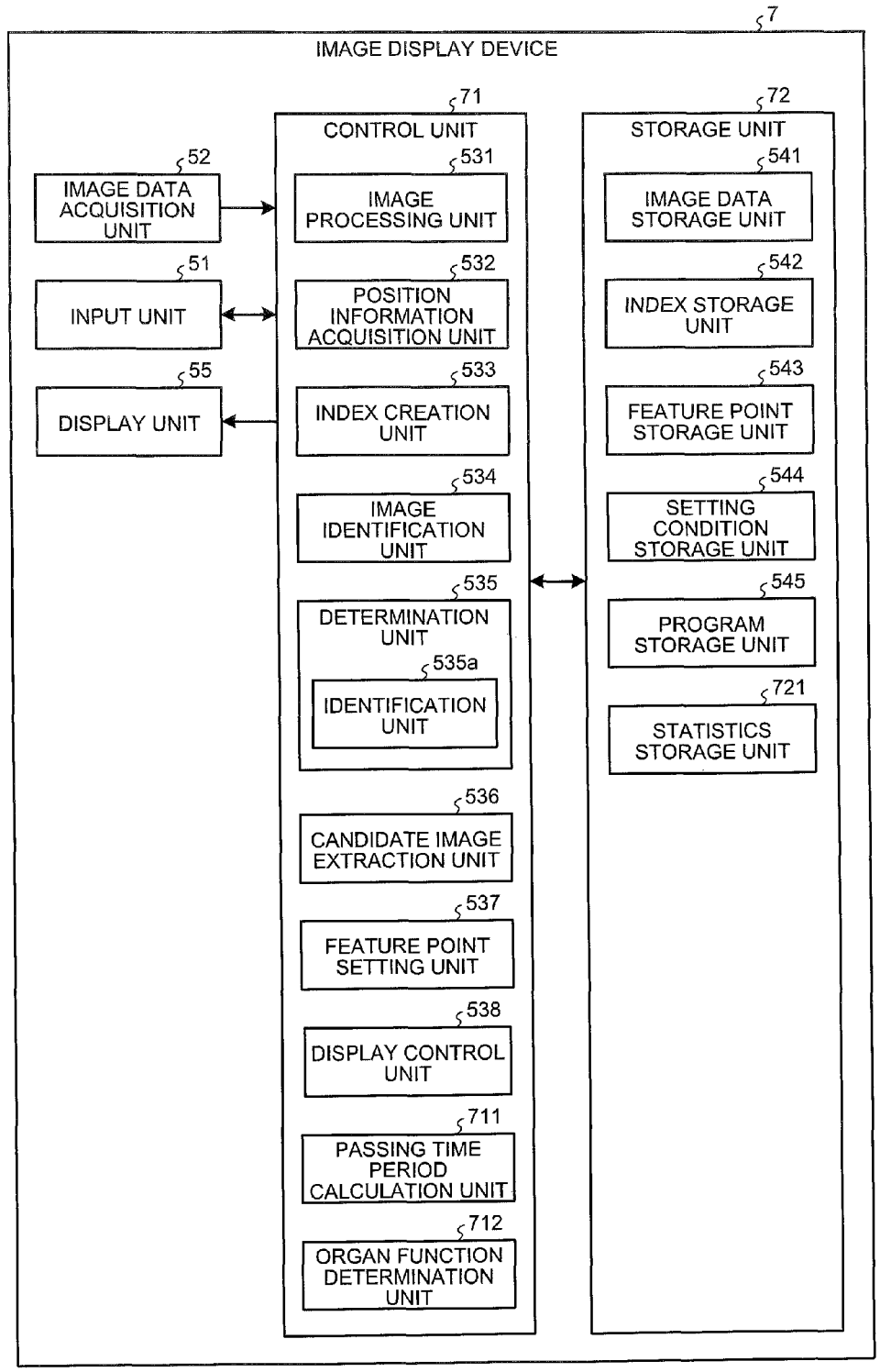
FIG. 14 is a block diagram illustrating a configuration of an image display device according to a fourth embodiment of the present invention.

Next, a fourth embodiment of the present invention will be described. A capsule endoscope system according to the fourth embodiment of the present invention includes an image display device 7 illustrated in FIG. 14 instead of the image display device 5 illustrated in FIG. 1. FIG. 14 is a block diagram illustrating a configuration of the image display device according to the fourth embodiment of the present invention. The image display device 7 illustrated in FIG. 14 includes a control unit 71 and a storage unit 72 instead of the control unit 53 and the storage unit 54 illustrated in FIG. 3.

The control unit 71 further includes a passing time period calculation unit 711 and an organ function determination unit 712 in addition to the components of the control unit 53 illustrated in FIG. 3. The passing time period calculation unit 711 calculates a passing time period of the capsule endoscope 2 between feature points different from each other. The organ function determination unit 712 determines a function of an organ in the subject based on the passing time period calculated by the passing time period calculation unit 711. A configuration and an operation of each unit in the control unit 71 other than the passing time period calculation unit 711 and the organ function determination unit 712 are the same as those in the first embodiment.

The storage unit 72 further includes a statistics storage unit 721 in addition to the components of the storage unit 54 illustrated in FIG. 3. The statistics storage unit 721 stores statistics of the passing time period of the capsule endoscope 2 in the subject for each type of organ such as stomach, small intestine, and large intestine. It is more preferable for the statistics storage unit 721 to accumulate statistics of the passing time period of the capsule endoscope 2 in each organ for each age, gender, and medical history of a patient who is the subject. As the statistics, any one of the average value, the mode value, and the median value may be used. A configuration of each unit in the storage unit 72 other than the statistics storage unit 721 are the same as those in the in the first embodiment.

Next, an operation of the image display device 7 will be described. In the same manner as in the first embodiment, the image display device 7 has a function to additionally perform function determination of an organ in the subject after performing transfer of image data from the receiving device 3 (see FIG. 5) and setting of a feature point (see FIG. 6). The image data transfer processing and the feature point setting processing performed by the image display device 7 are the same as those of the first embodiment. Alternatively, the feature point setting processing may be performed in the same manner as in the second and the third embodiments.

FIG. 15 is a flowchart illustrating organ function determination processing performed by the image display device 7. First, in step S60, the organ function determination unit 712 determines whether or not the entrance of the stomach and the entrance of the small intestine have been set as feature points on a series of images. When the entrance of the stomach and the entrance of the small intestine have not been set as feature points (step S60: No), the processing proceeds to step S65 described later.

On the other hand, when the entrance of the stomach and the entrance of the small intestine have been set as feature points (step S60: Yes), the passing time period calculation unit 711 calculates the time period for passing through the stomach of the capsule endoscope 2 (step S61). The time period for passing through the stomach is obtained by calculating a difference between the imaging time of the feature point image set as the entrance of the stomach and the imaging time of the feature point image set as the entrance of the small intestine.

In the following step S62, the organ function determination unit 712 reads a statistic of the time period for passing through the stomach from the statistics storage unit 721 and compares the time period for passing through the stomach calculated in step S61 with the statistic. When the time period for passing through the stomach calculated in step S61 is smaller than or equal to the statistic (step S63: No), the processing ends.

On the other hand, when the time period for passing through the stomach calculated in step S61 is longer than the statistic (step S63: Yes), it is considered that a function (peristaltic motion) of the stomach of the subject is weakened. In this case, the organ function determination unit 712 causes the display unit 55 to display a message indicating that the function of the stomach is weakened (step S64). A specific example of the message is "The time period for passing through the stomach is longer than usual. The function of the stomach may be weakened." and the like.

In the following step S65, the passing time period calculation unit 711 determines whether or not the entrance of the small intestine and the entrance of the large intestine have been set as feature points. When the entrance of the small intestine and the entrance of the large intestine have not been set as feature points (step S65: No), the processing ends.

On the other hand, when the entrance of the small intestine and the entrance of the large intestine have been set as feature points (step S65: Yes), the passing time period calculation unit 711 calculates the time period for passing through the small intestine of the capsule endoscope 2 (step S66). The time period for passing through the small intestine is obtained by calculating a difference between the imaging time of the feature point image set as the entrance of the small intestine and the imaging time of the feature point image set as the entrance of the large intestine.

In the following step S67, the organ function determination unit 712 reads a statistic of the time period for passing through the small intestine from the statistics storage unit 721 and compares the time period for passing through the small intestine calculated in step S66 with the statistic. When the time period for passing through the small intestine calculated in step S66 is smaller than or equal to the statistic (step S68: No), the processing ends.

On the other hand, when the time period for passing through the small intestine calculated in step S66 is longer than the statistic (step S68: Yes), it is considered that a function of the small intestine of the subject, specifically, the peristaltic motion, is weakened. In this case, the organ function determination unit 712 causes the display unit 55 to display a message indicating that the function of the small intestine is weakened (step S69). A specific example of the message is "The time period for passing through the small intestine is longer than usual. The function of the small intestine may be weakened." and the like. Thereafter, the processing ends.

As described above, according to the fourth embodiment of the present invention, it is possible to accurately calculate the time period for passing through each organ by the capsule endoscope 2 based on the appropriately set feature points. Therefore, when functional decline of an organ is predicted from a comparison result between the time period for passing through an organ and the statistic, by notifying a user accordingly, the user can perform image observation under consideration of the functional decline of the organ.

The present invention described above is not limited to the first to the fourth embodiments and the modified examples thereof, but various inventions can be formed by appropriately combining a plurality of components disclosed in the embodiments and the modified examples. For example, the inventions may be formed by removing some components from all the components described in each of the embodiments and the modified examples or may be formed by appropriately combining components described in different embodiments and modified examples.

In the above description, the first to the fourth embodiments of the present invention and the modified examples thereof are described assuming a case in which a capsule endoscope is used in the medical field. However, the embodiments and the modified examples may be applied in a case in which a capsule endoscope is used in fields other than the medical field.

According to some embodiments, it is determined whether or not an image selected by a user is an image acquired while a capsule endoscope makes a reciprocating movement. When it is determined that the image selected by the user is an image acquired while the capsule endoscope makes a reciprocating movement, an image that is more appropriate as an image to set a feature point is extracted from a series of images, and the image is displayed as a candidate image. Therefore, the user can easily set an appropriate feature point by referring to the candidate image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a processor comprising hardware, wherein the processor is configured to:
identify an identified image selected according to a first user input operation received by an input device, from among a plurality of first images acquired by a capsule endoscope;
identify a plurality of second images acquired by the capsule endoscope, each of the plurality of second images being captured at a position within a predetermined position range from an identified image capsule position where the identified image was captured by the capsule endoscope, from the plurality of first images;
acquire an imaging sequence of the plurality of second images;
acquire a plurality of capsule positions, each of the plurality of capsule positions being a position of the capsule endoscope when each of the plurality of second images is acquired;
determine from the imaging sequence of the plurality of second images and the plurality of capsule positions whether the capsule endoscope engaged in a reciprocating movement during the time period in which the plurality of second images were acquired by the capsule endoscope;
in response to determining that the capsule endoscope did not engage in the reciprocating movement, set the identified image as a feature point image; and
in response to determining that the capsule endoscope did engage in the reciprocating movement:
extract a plurality of candidate images in a first forward path or a last forward path of the reciprocating movement from among the plurality of second images; and
set an image selected according to a second user input operation received by the input device, from among the candidate images, as the feature point image.

2. The image processing device according to claim 1, wherein the processor is further configured to:
determine, from the imaging sequence of the plurality of second images and the plurality of capsule positions that whether the plurality of second images comprises two or more image groups which continue in a forward direction in time series as well as continue in a forward direction in position series; and
in response to determining that the plurality of second images comprises the two or more image groups which continue in the forward direction in time series as well as continue in a forward direction in position series, determine that the capsule endoscope engaged in the reciprocating movement during the time period in which the plurality of second images were acquired by the capsule endoscope.

3. The image processing device according to claim 1, wherein the processor is further configured to:
   acquire a plurality of capsule positions, each capsule position being a position of the capsule endoscope when each of the plurality of first images is acquired;
   identify a plurality of third images, each third image where the capsule position or an imaging time is within a predetermined range with respect to the identified image;
   determine a similarity between the identified image and each of the plurality of third images; and
   determine that the identified image is one of the plurality of second images when two or more image groups, which include an image that is determined to be similar to the identified image and in which image numbers are continuous, are included in the plurality of third images.

4. The image processing device according to claim 3, wherein the processor is further configured to extract an image determined to be similar to the identified image from among images acquired in the first forward path or the last forward path.

5. The image processing device according to claim 1, wherein the processor is further configured to control a display to display the feature point image.

6. An image processing method comprising:
   identifying an identified image selected according to a first user input operation received by an input device, from among a plurality of first images acquired by a capsule endoscope;
   identifying a plurality of second images acquired by the capsule endoscope, each of the plurality of second images being captured at a position within a predetermined position range from an identified image capsule position where the identified image was captured by the capsule endoscope, from the plurality of first images;
   acquiring an imaging sequence of the plurality of second images;
   acquiring a plurality of capsule positions, each of the plurality of capsule positions being a position of the capsule endoscope when each of the plurality of second images is acquired;
   determining from the imaging sequence of the plurality of second images and the plurality of capsule positions whether the capsule endoscope engaged in a reciprocating movement during the time period in which the plurality of second images were acquired by the capsule endoscope;
   in response to determining that the capsule endoscope did not engage in the reciprocating movement, setting the identified image as a feature point image; and
   in response to determining that the capsule endoscope did engage in the reciprocating movement:
      extracting a plurality of candidate images in a first forward path or a last forward path of the reciprocating movement from among the plurality of second images; and
      setting an image selected according to a second user input operation received by the input device, from among the candidate images, as the feature point image.

7. A non-transitory computer-readable recording medium recording an image processing program for causing an image processing device to execute:
   identifying an identified image selected according to a first user input operation received by an input device, from among a plurality of first images acquired by a capsule endoscope;
   identifying a plurality of second images acquired by the capsule endoscope, each of the plurality of second images being captured at a position within a predetermined position range from an identified image capsule position where the identified image was captured by the capsule endoscope, from the plurality of first images;
   acquiring an imaging sequence of the plurality of second images;
   acquiring a plurality of capsule positions, each of the plurality of capsule positions being a position of the capsule endoscope when each of the plurality of second images is acquired;
   determining from the imaging sequence of the plurality of second images and the plurality of capsule positions whether the capsule endoscope engaged in a reciprocating movement during the time period in which the plurality of second images were acquired by the capsule endoscope;
   in response to determining that the capsule endoscope did not engage in the reciprocating movement, setting the identified image as a feature point image; and
   in response to determining that the capsule endoscope did engage in the reciprocating movement:
      extracting a plurality of candidate images in a first forward path or a last forward path of the reciprocating movement from among the plurality of second images; and
      setting an image selected according to a second user input operation received by the input device, from among the candidate images, as the feature point image.

* * * * *